(12) United States Patent
Daley et al.

(10) Patent No.: US 6,534,149 B1
(45) Date of Patent: *Mar. 18, 2003

(54) INTAKE/DISTRIBUTION MATERIAL FOR PERSONAL CARE PRODUCTS

(75) Inventors: Michael Allen Daley, Alpharetta, GA (US); Yvette Lynn Hammonds, Fond du Lac, WI (US); Tamara Lee Mace, Doraville, GA (US); David Michael Matela, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/500,498

(22) Filed: Feb. 9, 2000

Related U.S. Application Data (60) Provisional application No. 60/127,682, filed on Apr. 3, 1999.

(51) Int. Cl.$^7$ .............................................. A61F 13/513
(52) U.S. Cl. ...................... 428/137; 428/131; 428/138; 604/378; 604/383
(58) Field of Search ............................... 428/137, 138, 428/131; 604/378, 383

(56) References Cited

U.S. PATENT DOCUMENTS

| | | | |
|---|---|---|---|
| 3,029,817 A | 4/1962 | Harwood et al. | 128/290 |
| 3,338,992 A | 8/1967 | Kinney | 264/24 |
| 3,341,394 A | 9/1967 | Kinney | 161/72 |
| 3,375,448 A | 3/1968 | Newman et al. | 328/42 |
| 3,502,763 A | 3/1970 | Hartmann | 264/210 |
| 3,542,615 A | 11/1970 | Dobo et al. | 156/181 |
| 3,667,468 A | 6/1972 | Nystrand et al. | 128/290 |
| 3,692,618 A | 9/1972 | Dorschner et al. | 161/72 |
| 3,749,627 A | 7/1973 | Jones, Sr. | 156/268 |

(List continued on next page.)

FOREIGN PATENT DOCUMENTS

| | | | |
|---|---|---|---|
| CA | 1128704 | 8/1982 | |
| DE | 19609462 | 9/1997 | ............ A61F/13/46 |
| EP | 0 124 365 | 11/1984 | ............ A61F/13/00 |
| GB | 2 111 836 | 7/1983 | ............ A61F/13/16 |
| JP | 8164160 | 6/1996 | |
| WO | 95/07673 | 3/1995 | ............ A61F/13/15 |
| WO | 95/10996 | 4/1995 | ............ A61F/13/46 |
| WO | 95/17870 | 7/1995 | ............ A61F/13/15 |
| WO | 96/33679 | 10/1996 | ............ A61F/13/15 |
| WO | 97/14384 | 4/1997 | ............ A61F/13/15 |
| WO | 97/18783 | 5/1997 | ............ A61F/13/15 |
| WO | 97/36565 | 10/1997 | ............ A61F/13/46 |
| WO | 97/45083 | 12/1997 | ............ A61F/13/15 |
| WO | 98/13003 | 4/1998 | ............ A61F/13/15 |
| WO | 98/22065 | 5/1998 | ............ A61F/13/15 |
| WO | 98/24960 | 6/1998 | ............ D04H/1/54 |

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

"Quantification of Unidirectional Fiber Bed Permeability" by J. Westhuizen and J. P. Du Plessis in the *Journal of Composite Materials*, 28(7), 1994.

Primary Examiner—William P. Watkins, III
(74) Attorney, Agent, or Firm—Steven D. Flack (57) ABSTRACT

There is provided an intake/distribution layer for personal care products which is a co-apertured distribution layer and a transfer delay layer between them. The co-apertured distribution and transfer delay layer can serve to store liquid and release it to an absorbent core in a personal care product at a rate at which the core can absorb. This ability to accept irregular and large flow rates makes the layer of this invention particularly well suited for "gush" management. The distribution layer is preferably an airlaid fabric and the transfer delay layer is preferably a spunbond fabric and they are co-apertured using a pin density of preferably about 2.5 pins/cm$^2$.

17 Claims, 6 Drawing Sheets

U.S. PATENT DOCUMENTS

| | | | | |
|---|---|---|---|---|
| 3,802,817 A | 4/1974 | Matsuki et al. ................ 425/66 |
| 3,849,241 A | 11/1974 | Butin et al. .................. 161/169 |
| 3,855,046 A | 12/1974 | Hansen et al. ............... 161/150 |
| 3,860,002 A | 1/1975 | Kolbach ..................... 128/284 |
| 3,871,378 A | 3/1975 | Duncan et al. .............. 128/290 |
| 3,897,784 A | 8/1975 | Fitzgerald ................ 128/290 R |
| 4,016,628 A | 4/1977 | Kolbach ........................ 19/148 |
| 4,027,672 A | 6/1977 | Karami ....................... 128/284 |
| 4,093,765 A | 6/1978 | Schmidt ...................... 428/134 |
| 4,100,324 A | 7/1978 | Anderson et al. ............ 428/288 |
| RE29,789 E | 10/1978 | Kolbach ...................... 128/284 |
| 4,340,563 A | 7/1982 | Appel et al. ................. 264/518 |
| 4,494,278 A | 1/1985 | Kroyer et al. ................. 19/304 |
| 4,614,679 A | 9/1986 | Farrington, Jr. et al. ..... 428/138 |
| 4,636,209 A | 1/1987 | Lassen ........................ 604/378 |
| 4,640,810 A | 2/1987 | Laursen et al. .............. 264/518 |
| 4,795,455 A | 1/1989 | Luceri et al. ................ 604/386 |
| 4,818,464 A | 4/1989 | Lau ............................. 264/510 |
| 4,988,344 A | 1/1991 | Reising et al. ............... 604/368 |
| 5,047,023 A | 9/1991 | Berg .......................... 604/368 |
| 5,057,368 A | 10/1991 | Largman et al. ............. 428/397 |
| 5,069,970 A | 12/1991 | Largman et al. ............. 428/373 |
| 5,108,820 A | 4/1992 | Kaneko et al. .............. 428/198 |
| 5,108,827 A | 4/1992 | Gessner ...................... 428/219 |
| 5,147,345 A | 9/1992 | Young et al. ................. 604/378 |
| 5,231,122 A | 7/1993 | Palumbo et al. ............... 524/30 |
| 5,277,976 A | 1/1994 | Hogle et al. ................. 428/397 |
| 5,281,208 A | 1/1994 | Thompson et al. .......... 604/378 |
| 5,300,054 A | 4/1994 | Feist et al. ................... 604/378 |
| 5,304,161 A | 4/1994 | Noel et al. ................... 604/378 |
| 5,318,554 A | 6/1994 | Young et al. ................. 604/378 |
| 5,330,456 A | 7/1994 | Robinson .................... 604/368 |
| 5,336,552 A | 8/1994 | Strack et al. ................ 428/224 |
| 5,348,547 A | 9/1994 | Payne et al. ................. 604/378 |
| 5,364,382 A | 11/1994 | Latimer et al. .............. 604/378 |
| 5,366,451 A | 11/1994 | Levesque .................... 604/378 |
| 5,374,260 A | 12/1994 | Lemay et al. ................ 604/378 |
| 5,382,400 A | 1/1995 | Pike et al. ................... 264/168 |
| 5,397,316 A | 3/1995 | LaVon et al. ................ 604/369 |
| 5,429,629 A | 7/1995 | Latimer et al. .............. 604/378 |
| 5,437,653 A | 8/1995 | Gilman et al. ............... 604/378 |
| 5,439,458 A | 8/1995 | Noel et al. ................... 604/378 |
| 5,454,800 A | 10/1995 | Hirt et al. .................... 604/378 |
| 5,460,622 A | 10/1995 | Dragoo et al. ............... 604/378 |
| 5,466,232 A | 11/1995 | Cadieux et al. .............. 604/378 |
| 5,466,410 A | 11/1995 | Hills ....................... 264/172.11 |
| 5,466,513 A | 11/1995 | Wanek et al. ................ 428/218 |
| 5,476,711 A | 12/1995 | Hebbard et al. ............. 428/283 |
| 5,486,167 A | 1/1996 | Dragoo et al. ............... 604/384 |
| 5,514,104 A | 5/1996 | Cole et al. ................... 604/366 |
| 5,527,171 A | 6/1996 | Soerensen ................... 425/83.1 |
| 5,549,589 A | 8/1996 | Horney et al. ............... 604/366 |
| 5,558,655 A | 9/1996 | Jezzi et al. ................... 604/378 |
| 5,562,650 A | 10/1996 | Everett et al. ............... 604/378 |
| 5,603,707 A | 2/1997 | Trombetta et al. ........... 604/383 |
| 5,607,414 A | 3/1997 | Richards et al. ............. 604/378 |
| 5,634,915 A | 6/1997 | Osterdahl .................... 604/379 |
| 5,647,862 A | 7/1997 | Osborn, III et al. ......... 604/378 |
| 5,647,863 A | 7/1997 | Hammons et al. ........... 604/378 |
| 5,649,916 A | 7/1997 | DiPalma et al. .............. 604/378 |
| 5,662,633 A | 9/1997 | Doak et al. .................. 604/378 |
| 5,665,082 A | 9/1997 | Boulanger ................... 604/365 |
| 5,669,895 A | 9/1997 | Murakami et al. ........... 604/380 |
| 5,695,487 A | 12/1997 | Cohen et al. ................ 604/384 |
| 5,728,085 A | 3/1998 | Widlund et al. ............. 604/378 |
| 5,730,737 A | 3/1998 | Widlund et al. ............. 604/378 |
| 5,785,697 A | 7/1998 | Trombetta et al. ........... 604/378 |
| 5,797,894 A | 8/1998 | Cadieux et al. .............. 604/378 |
| 5,807,362 A | 9/1998 | Serbiak et al. ............... 604/361 |
| 5,817,394 A | * 10/1998 | Alikhan et al. .............. 428/137 |

\* cited by examiner

INTAKE/DISTRIBUTION MATERIAL FOR PERSONAL CARE PRODUCTS

This application claims priority from U.S. Provisional Patent Application No. 60/127,682 filed Apr. 3, 1999.

FIELD OF THE INVENTION

The present invention relates to a structure in an article for personal care like diapers, training pants, absorbent underpants, adult incontinence products, bandages and feminine hygiene products, which can accept and distribute liquid.

BACKGROUND OF THE INVENTION

Personal care articles include such items as diapers, training pants, feminine hygiene products such as sanitary napkins, panty-liners and tampons, incontinence garments and devices, bandages and the like. The most basic design of all such articles typically includes a bodyside liner, an outercover and an absorbent core disposed between the bodyside liner and the outercover.

Personal care products must accept fluids quickly and hold them to reduce the possibility of leakage outside the product. The product must be flexible and have a pleasing feel on the skin, and even after liquid insult, must not become tight or bind the user. Unfortunately, while previous products have met many of these criteria to varying degrees, a number have not.

It has been found that continuous flow insults in feminine hygiene products average 1 ml/hr and are not literally continuous or constant, but rather variable in rate and may even pause during a cycle. "Gush flow" is defined as a sudden heavy flow condition and occurs at flow rates of up to 1 ml/sec. During a gush, 1–5 ml of fluid is released from the body onto the product. The term "continuous flow" is used to define any flow which falls outside of the definition of gush flow.

Figure 1:
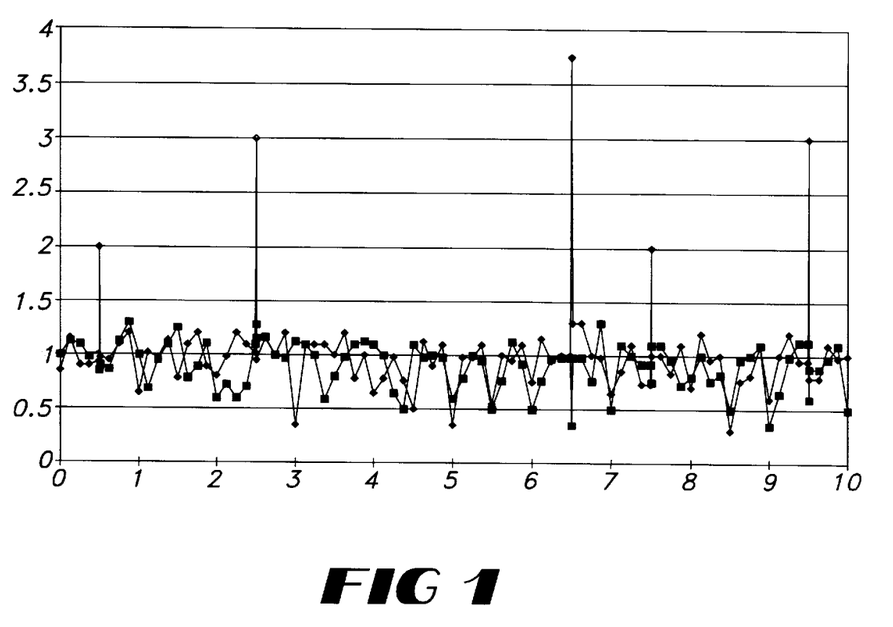
FIG. 1 is a graph of variable flow (diamonds) and continuous flow (squares) over the life of a single product where flow rate volume is on the y-axis in g/hr and time is on the x-axis in hours.

Combining continuous and gush flow conditions results in variable flow. Essentially, "variable flow" is defined as continuous flow with intermittent gush flow occurrences. FIG. 1 illustrates the differences between variable flow (diamonds) and continuous flow (squares) over the life of a single product where flow rate volume is on the y-axis in g/hr and time is on the x-axis in hours.

The response to this problem is termed "variable flow management" and is defined as the ability to absorb and contain continuous and light flow (1–2 ml/hr) as well as multiple gushes or sudden heavy flow insults (1 ml/sec with a total volume of 1–5 ml) over the life of the product.

Many feminine care cover materials, for example, have low z-directional conductivity, low surface energy, low void volume, and provide little separation between the absorbent core and the user due to their two dimensional structure. Consequently, these covers result in slow and incomplete intake, high rewet, and large surface stains. In addition, typical intake or acquisition layers are low density, high void volume structures which are ideal for fast fluid intake, but because these structures typically have low capillarity, fluid is not adequately desorbed from the cover material, resulting in smearing and surface wetness. Materials which enhance cover desorption are typically high density, high capillarity materials, but because these materials have low void volume and low z-directional permeability, they inherently retard fluid intake.

There remains a need to address variable flow management by developing on an intake/distribution material which has the void volume necessary for fast intake and the high capillarity desired for sufficient cover desorption (i.e. surface dryness) while maintaining an appropriate capillary structure for fluid distribution.

An objective of this invention is, therefore, to provide such an intake/distribution material to manage a wide variety of flow conditions including sudden heavy flow insults, or gushes.

SUMMARY OF THE INVENTION

The objects of the invention are achieved by a airlaid fabric layer and spunbond nonwoven fabric transfer delay layer which have been joined by aperturing or "co-apertured". The result is improved multiple intake performance and a clean and dry cover surface during use in a feminine hygiene product. The material technology developments surrounding variable flow management focus on attaining the proper material structure and property balance necessary to achieve fast intake and improve cover desorption, cover staining, and rewet characteristics. These functional properties are provided through improved material technologies and product construction.

BRIEF DESCRIPTION OF THE DRAWINGS

FIGS. 3, 4, and 5 display SEM images of the apertures.

DEFINITIONS

"Disposable" includes being disposed of after use and not intended to be washed and reused.

"Hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic.

"Layer" when used in the singular can have the dual meaning of a single element or a plurality of elements.

"Liquid" means a non-particulate substance and/or material that flows and can assume the interior shape of a container into which it is poured or placed.

"Liquid communication" means that liquid is able to travel from one layer to another layer, or one location to another within a layer.

"Conjugate fibers" refers to fibers that have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al., and U.S. Pat. Nos. 5,069,970 and 5,057,368 to Largman et al., hereby incorporated by reference in their entirety, which describe fibers with unconventional shapes.

"Biconstituent fibers" refers to fibers that have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein, the term "machine direction" or MD means the length of a fabric in the direction in which it is produced. The term "cross machine direction" or CD means the width of fabric, i.e. a direction generally perpendicular to the MD.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 35 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers that may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be pulp, superabsorbent or other particles, natural polymers (for example, rayon or cotton fibers) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

"Bonded carded web" refers to webs that are made from staple fibers that are sent through a combing or carding unit, which breaks apart and aligns the staple fibers in the machine direction to form a generally machine direction-oriented fibrous nonwoven web. The web is bonded by one or more of several known bonding methods.

"Airlaying" is a well-known process by which a fibrous nonwoven layer can be formed. In the airlaying process, bundles of small fibers having typical lengths ranging from about 3 to about 52 millimeters are separated and entrained in an air supply and then deposited onto a forming screen, usually with the assistance of a vacuum supply. The randomly deposited fibers then are bonded to one another using, for example, hot air or a spray adhesive. Examples of airlaying technology can be found in U.S. Pat. Nos. 4,494,278, 5,527,171, 3,375,448 and 4,640,810.

Bonding of nonwoven webs may be achieved by a number of methods; powder bonding, wherein a powdered adhesive is distributed through the web and then activated, usually by heating the web and adhesive with hot air; pattern bonding, wherein heated calender rolls or ultrasonic bonding equipment are used to bond the fibers together, usually in a localized bond pattern, though the web can be bonded across its entire surface if so desired; through-air bonding, wherein air which is sufficiently hot to soften at least one component of the web is directed through the web; chemical bonding using, for example, latex adhesives that are deposited onto the web by, for example, spraying; and consolidation by mechanical methods such as needling and hydroentanglement.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

"Co-aperture" refers to a material which has been apertured, as well as a process of aperturing, wherein two or more materials are apertured together. The apertures extend from top to bottom of the material and are essentially aligned with each other. Co-aperturing can join the materials either temporarily or permanently through entanglement, physical bonding or chemical bonding. It is preferred that co-aperturing be carried out at ambient temperatures, not at elevated temperatures.

"Personal care product" means diapers, training pants, absorbent underpants, adult incontinence products, swim wear, bandages and other wound dressings, and feminine hygiene products.

"Feminine hygiene products" means sanitary napkins, pads and tampons.

"Target area" refers to the area or position on a personal care product where an insult is normally delivered by a wearer.

TEST METHODS

Material Caliper (thickness):

The caliper of a material is a measure of thickness and is measured at 0.05 psi (3.5 g/cm$^2$) with a Starret-type bulk tester, in units of millimeters.

Density:

The density of the materials is calculated by dividing the weight per unit area of a sample in grams per square meter (gsm) by the material caliper in millimeters (mm) at 0.05 psi (3.5 g/cm$^2$) and multiplying the result by 0.001 to convert the value to grams per cubic centimeter (g/cc). A total of three samples would be evaluated and averaged for the density values.

Horizontal Capillary Wicking Test Procedure:

The objective of this test it to determine the horizontal wicking capability of a material as it pulls fluid from a infinite reservoir.

Equipment needed: Horizontal wicking stand, menses simulant prepared as described below, ruler, timer.

Procedure:

Cut materials to 1" (2.54 cm) width and desired length.

Fill reservoir in horizontal wicking apparatus with menses simulant.

Place one end of the material in the simulant and lay the rest of the material on the wicking apparatus.

Start the timer.

Measure the distance wicked at a given time, or the time to wick to a given distance.

Preparation of Menses Simulant:

In order to prepare the fluid, blood, in this case defibrinated swine blood, was separated by centrifugation at 3000 rpm for 30 minutes, though other methods or speeds and times may be used if effective. The plasma was separated and stored separately, the buffy coat removed and discarded and the packed red blood cells stored separately as well.

Eggs, in this case jumbo chicken eggs, were separated, the yolk and chalazae discarded and the egg white retained. The egg white was separated into thick and thin portions by straining the white through a 1000 micron nylon mesh for about 3 minutes, and the thinner portion discarded. Note that alternative mesh sizes may be used and the time or method may be varied provided the viscosity is at least that required. The thick portion of egg white which was retained on the mesh was collected and drawn into a 60 cc syringe which was then placed on a programmable syringe pump and homogenized by expelling and refilling the contents five times. In this example, the amount of homogenization was controlled by the syringe pump rate of about 100 ml/min, and the tubing inside diameter of about 0.12 inches. After homogenizing the thick egg white had a viscosity of about 20 centipoise at 150 sec$^{-1}$ and it was then placed in the centrifuge and spun to remove debris and air bubbles at about 3000 rpm for about 10 minutes, though any effective method to remove debris and bubbles may be used.

After centrifuging, the thick, homogenized egg white, which contains ovamucin, was added to a 300 cc Fenwal® Transfer pack using a syringe. Then 60 cc of the swine plasma was added to the transfer pack. The transfer pack was clamped, all air bubbles removed, and placed in a Stomacher lab blender where it was blended at normal (or medium) speed for about 2 minutes. The transfer pack was then removed from the blender, 60 cc of swine red blood cells were added, and the contents mixed by hand kneading for about 2 minutes or until the contents appeared homogenous. A hematocrit of the final mixture showed a red blood cell content of about 30 weight percent and generally should be at least within a range of 28–32 weight percent for artificial menses made according to this example. The amount of egg white was about 40 weight percent.

The ingredients and equipment used in the preparation of this artificial menses are readily available. Below is a listing of sources for the items used in the example, though of course other sources may be used providing they are approximately equivalent.

Blood (swine): Cocalico Biologicals, Inc., 449 Stevens Rd., Reamstown, Pa. 17567, (717) 336–1990.

Fenwal® Transfer pack container, 300 ml, with coupler, sample 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-242.

Hemata Stat-II device to measure hemocrits, serial no. 1194Z03127: Separation Technology, Inc., 1096 Rainer Drive, Altamont Springs, Fla. 32714.

DETAILED DESCRIPTION OF THE INVENTION

The instant invention is an airlaid fabric distribution layer and spunbond nonwoven fabric transfer delay layer which have been joined by aperturing. Note that while airlaid and spunbond fabrics are preferred in the practice of this invention, other fabrics such as meltblown, coform, and bonded carded webs may be used in the practice of this invention provided they perform equivalently. Various foams may also be used, provided their performance is equivalent. Film may also be used, particularly as the transfer delay layer, and is used in some of the Examples below.

The airlaid distribution layer may be made from a variety of fibers and mixtures of fibers including synthetic fibers, natural fibers including hydroentangled pulp, mechanically and chemically softened pulp, staple fibers, slivers, meltblown and spunbond fibers and the like. The fibers in such a web may be made from the same or varying diameter fibers and may be of different shapes such as pentalobal, trilobal, elliptical, round, etc. The airlaid process is described above.

The spunbond transfer delay layer may also be made from a variety of fibers in a variety of shapes and sizes.

Binders may also be included in the spunbond or airlaid layers in order to provide mechanical integrity to the web. Binders include fiber, liquid or other binder means which may be thermally activated. Preferred fibers for inclusion are those having a relatively low melting point such as polyolefin fibers. Lower melting polymers provide the ability to bond the fabric together at fiber cross over points upon the application of heat. In addition, fibers having as at least one component a lower melting polymer, like conjugate and biconstituent fibers, are suitable for the practice of this invention. Fibers having a lower melting polymer are generally referred to as "fusible fibers." By "lower melting polymers" what is meant are those having a glass transition temperature less than about 175° C. Exemplary binder fibers include conjugate fibers of polyolefins and/or polyamides, and liquid adhesives. Two such suitable binders are sheath core conjugate fibers available from KoSA Inc. under the designation T-255 and T-256, though many suitable binder fibers are known to those skilled in the art, and are made by many manufacturers such as Chisso and Fibervisions LLC of Wilmington, Del. A suitable liquid binder is Kymene® 557LX binder available from Fibervisions LLC.

Synthetic fibers include those made from polyamides, polyesters, rayon, polyolefins, acrylics, superabsorbents, Lyocel regenerated cellulose and any other suitable synthetic fibers known to those skilled in the art. Synthetic fibers may also include kosmotropes for product degradation.

Many polyolefins are available for fiber production, for example polyethylenes such as Dow Chemical's ASPUN® 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's Escorene® PD 3445 polypropylene and Montell Chemical Co.'s PF-304. Many other polyolefins are commercially available.

Natural fibers include wool, cotton, flax, hemp and wood pulp. Pulps include standard soft-wood fluffing grade such as CR-1654 from Coosa Mills of Coosa, Ala., high bulk additive formaldehyde free pulp (HBAFF) available from the Weyerhaeuser Corporation of Tacoma, Wash., and is a which is a crosslinked southern softwood pulp fiber with enhanced wet modulus, and a chemically cross-linked pulp fiber such as Weyerhaeuser NHB416. HBAFF has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Courtaulds Fibers Incorporated of Axis, Ala.

The airlaid distribution layer and the spunbond transfer delay layer are co-apertured using mechanical pin aperturing. The co-aperturing of the distribution and transfer delay layers provides unique characteristics for the management of gush insults. A unique material is created with a tri-modal pore structure consisting of 1) pores in the bulk of the airlaid which are characteristic of the original airlaid structure, 2) large void spaces defined by the pins of the aperturing process, and 3) small interfacial pores surrounding the perimeter of the apertures. The apertures are typically characterized by an open structure which tapers into a rounded cone-like structure as observed from the airlaid side of the composite. The interfacial pores are smaller than the surrounding pores due to densification and fiber relocation which results from the aperturing process.

The transfer delay layer provides a permeability and wettability gradient between the airlaid distribution layer and the underlying retention layer in a feminine hygiene product by preventing intimate contact between the two layers. Since the transfer delay layer is non-wettable and has low permeability, it promotes fluid distribution in the airlaid layer under continuous flow conditions. The wettability of the transfer delay layer may be modified by topical chemical treatments known to those skilled in the art to affect the hydrophobicity of a material. Some suitable chemicals for modification of wettability are marketed under the tradenames AHCOVEL®, Glucopon®, Pluronics®, Triton®, and Masil SF-19®.

The transfer delay layer also controls fluid movement in the Z-direction. The transfer delay promotes fluid accumulation or hold-up in the airlaid distribution layer and then allows fluid transfer to the fluff when high pressures or high saturation levels occur. It is believed that fluid does not preferentially move into the apertures under continuous flow conditions. This controlled transfer mechanism results in an elongated stain pattern in the fluff and prevents over saturation in the insult area. Under gush flow conditions, the apertures in the transfer delay layer allow fluid to immediately pass through to the underlying fluff layer. Additionally, the transfer delay layer allows a visual signal to be incorporated into the product form.

Figure 2:
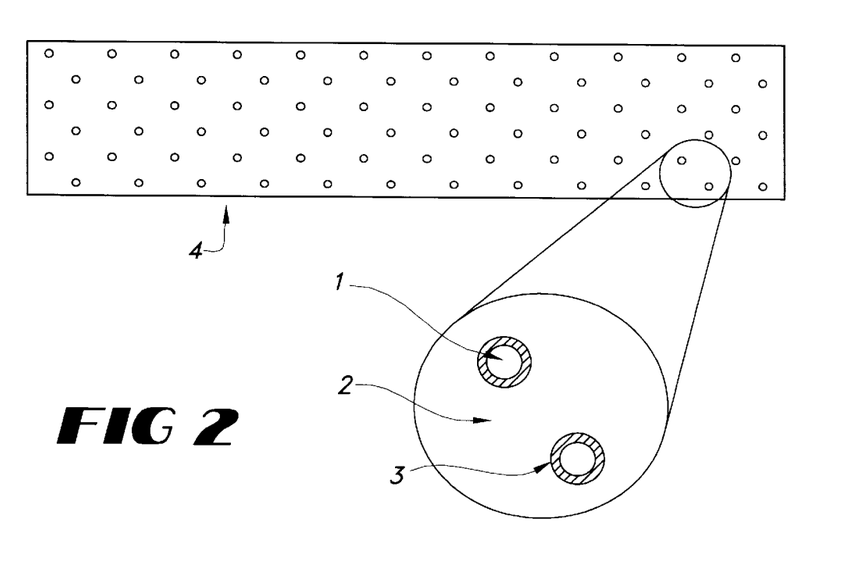
FIG. 2 illustrates the tri-modal pore structure of the co-apertured material.

FIG. 2 illustrates the tri-modal pore structure of the co-apertured material. In FIG. 2, three classes of pores are illustrated. Large pores 1 are located at the point where the fabric was apertured. Smaller pores 2 exist in the original airlaid fabric 4. Yet another class of pores 3 may be found in the area surrounding the point where the fabric was apertured due to densification of the fabric and fiber relocation during the aperturing process.

Figure 3:
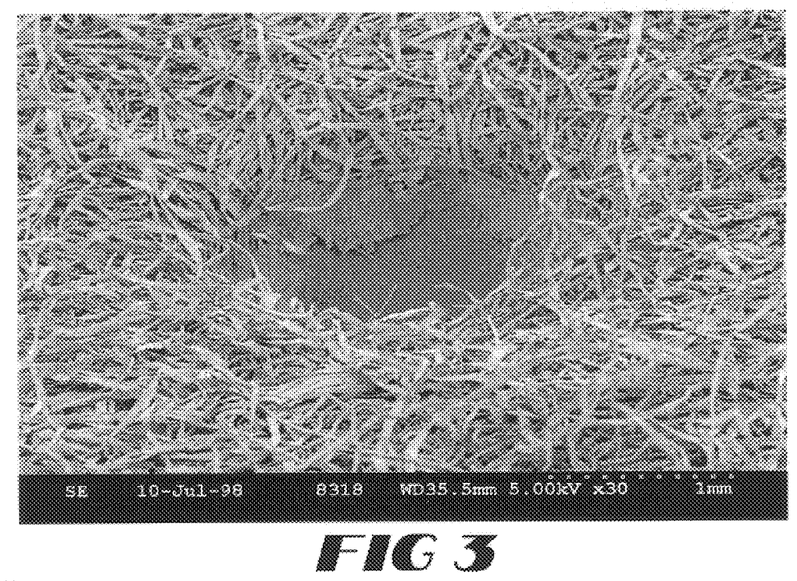
FIG. 3 displays an aperture on the airlaid side of the composite.
Figure 4:
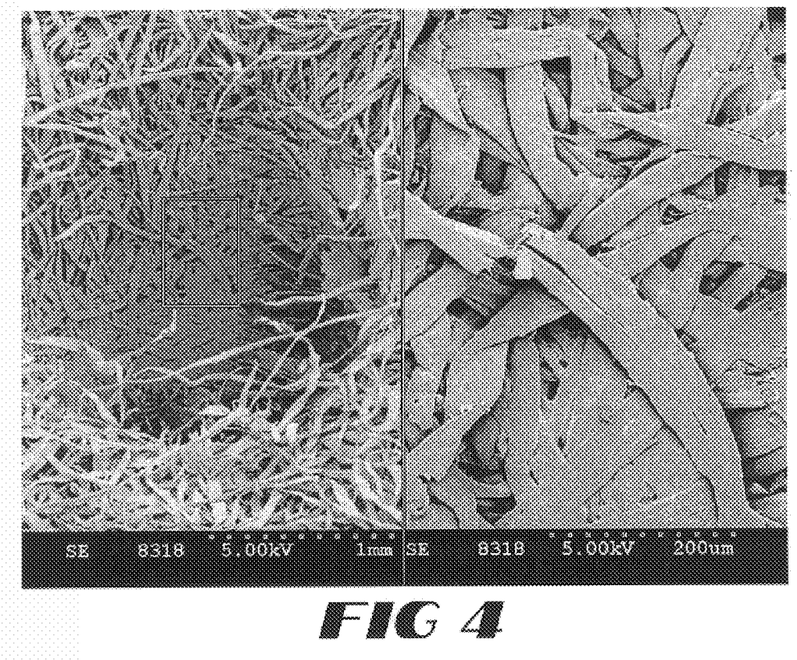
FIG. 4 displays a close-up of an aperture on the airlaid side of the composite and FIG. 5 displays an aperture from the spunbond side of the composite.
Figure 5:
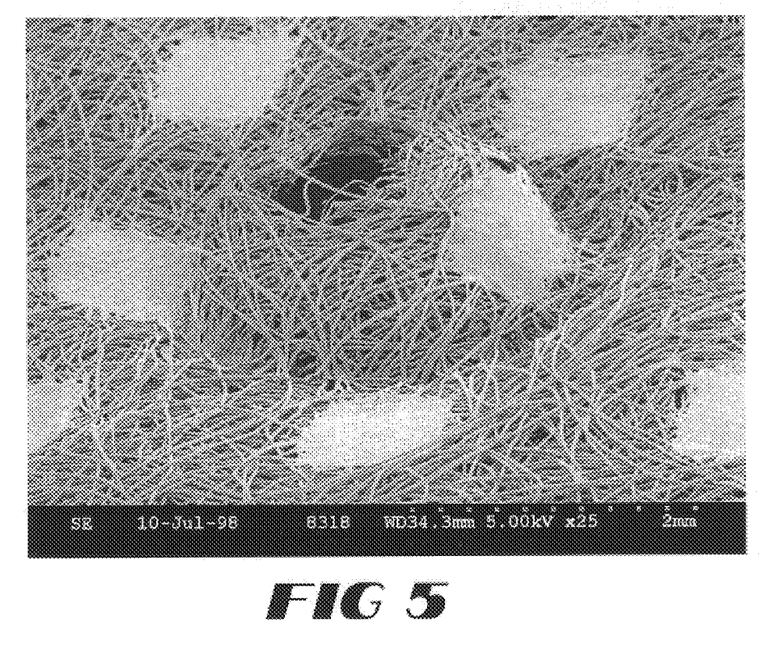

FIGS. 3, 4, and 5 display SEM images of the apertures. FIG. 3 displays an aperture on the airlaid side of the composite at a magnification of one inch (2.54 cm) equals 1 mm. FIG. 4 displays a close-up of an aperture on the airlaid side of the composite at a magnification of one inch equals 200 microns and FIG. 5 displays an aperture from the spunbond side of the composite at a magnification of one inch equals 2 mm.

Figure 6:
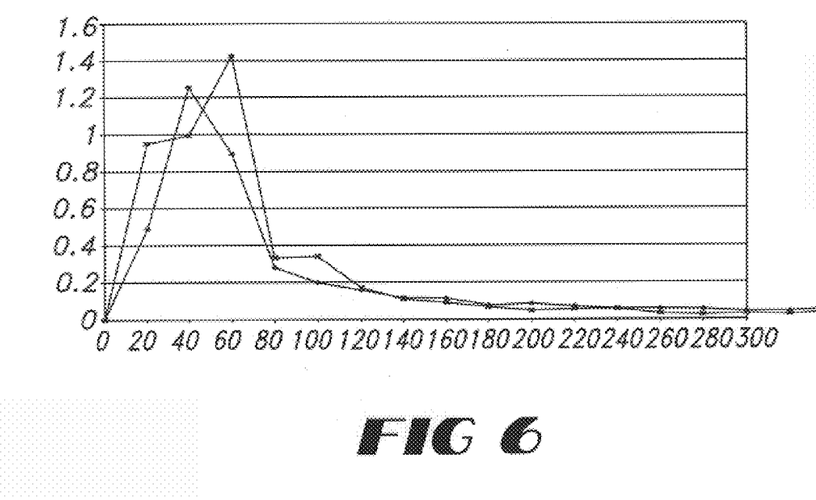
FIG. 6 compares the pore size distribution of an apertured airlaid material to a un-apertured airlaid material.

FIG. 6 compares the pore size distribution of an apertured airlaid material to a un-apertured airlaid material. In FIG. 6 the un-apertured airlaid material is signified by the large dark squares and the apertured airlaid material by the lighter colored diamonds. The pore volume (cc/g) is on the Y-axis and the pore radius (microns) on the X-axis. This graph indicates that there is a slight shift toward smaller pores with the apertured material. This is due to a slight densification of the material around the apertures. The large pores which are created by the apertures are not represented in the graph due to their large size. They do, however, provide additional void volume for the material.

Figure 7:
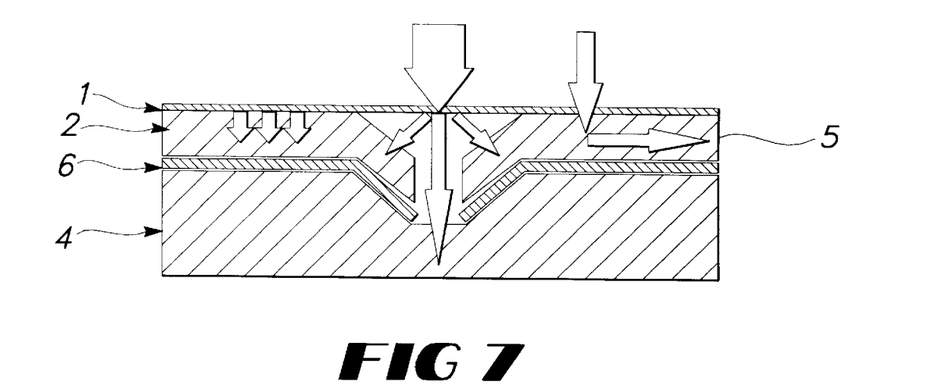
FIG. 7 illustrates the detail of a single aperture and the flow through the material.

FIG. 7 illustrates the detail of a single aperture in relation to the functionality of the absorbent composite. In FIG. 7 an insult (noted by arrows) is delivered to a cover 1. The insult flows through the cover 1 to the co-apertured laminate of the invention where it passes though the airlaid layer 2 either at the aperture 3 or through the airlaid layer 2 itself. The insult may also be distributed along its length to other areas 5 within the airlaid layer 2. Much of the insult eventually passes through the airlaid distribution layer 2 and transfer delay layer 6 to the absorbent retention core 4.

The functionality of the co-apertured system can be broken down into five areas: cover desorption, increased surface area, aperture void volume, access to fluff, and wicking capability. Each of these functionality benefits is discussed individually below.

1. Cover Desorption

The un-apertured areas of the airlaid material maintain a high degree of capillarity after insult and are well suited for desorbing a cover layer. The small pores of the airlaid material provide the capillarity necessary to desorb the typically large pores of a cover, thereby removing a majority of fluid from the surface of the product. Improved cover desorption results in low smearing and cover staining levels.

2. Increased Surface Area

The apertured areas of the airlaid material provide increased surface area for the absorption of fluid. During gush insults, fluid that contacts an aperture can be absorbed in the x, y, and z directions through the wall of the aperture, rather than strictly in the z-direction through the top surface. Therefore, the increased surface area provided by the walls of the apertures enhances the intake characteristics of the airlaid distribution layer. Additionally, the apertures increase the overall permeability of the airlaid distribution layer.

3. Aperture Void Volume

The open areas and void volume created by the apertures allow fluid to be accumulated internally in the product before absorption into the airlaid material. This prevents pooling on the product surface and facilitates intake when localized saturation of the airlaid prohibits immediate fluid intake.

4. Access to Retention

The apertures in the airlaid material provide a direct fluid pathway to the retention material in the apertured areas. Under gush flow conditions, fluid passes directly through the aperture and into the retention material. By providing immediate access to retention capacity under these conditions, the void volume of the airlaid is maintained and intake times for multiple insults are reduced.

5. Wicking Capability

Due to the airlaid material's stability and high degree of wet integrity, the pores do not collapse to an appreciable degree when a product is insulted. The stable pore structure allows capillary wicking to transport the fluid out of the insult area and into other regions of the product. The un-apertured areas of the airlaid material maintain this functionality and capillary wicking prevents high saturation from occurring in the insult area. Capillary wicking in combination with the stability of the material allows void volume to be regenerated after an insult so that additional insults can be accepted. A suitable intake/distribution layer horizontally wicks menses a distance of from about 1.2 cm to about 15.25 cm.

Experiments were undertaken to examine preferred forms of the invention. Three different basis weights of airlaid fabrics were evaluated: 100, 175, and 250 gsm. Comparisons were made between the three apertured airlaid fabric samples and an un-apertured control sample. Airlaid fabrics were made from Weyerhaeuser NB416 pulp and KoSa T-255 binder fiber. The spunbond layers were made from E5D47 polypropylene from the Union Carbide Company.

The spunbond layer was point bonded, in this case with an expanded Hansen Pennings (EHP) pattern. The separately produced airlaid and spunbond layers were put together and apertured at the noted pin density. Alternatively, its believed that the airlaid layer could be produced directly onto the spunbond layer and the two then apertured.

Figure 8:
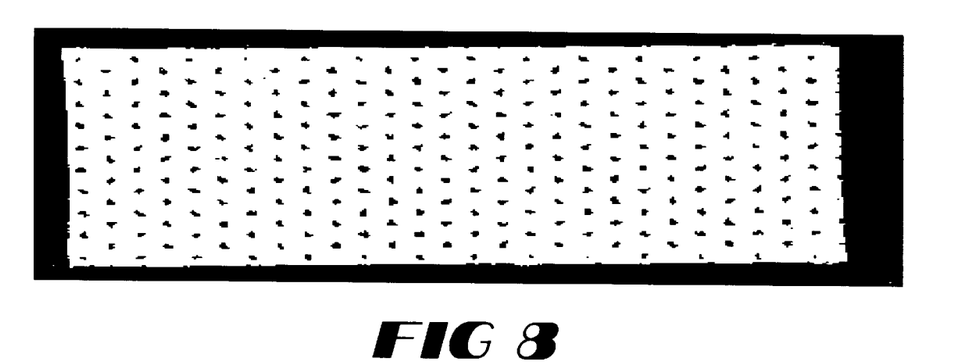
FIG. 8 shows the pin aperturing pattern at 7.4 pins/cm$^2$ using 2.06 mm diameter pins.

The aperturing pattern in FIG. 8 was used initially and had 48 pins/inch$^2$ (7.4 pins/cm$^2$) using 0.081" (2.06 mm) diameter pins.

These materials were tested over a pulp fluff absorbent core using the flat system fluid distribution test. Key measurements included stain size, whether the saturation profile was even or skewed, and the amount of fluid retention and transfer in the airlaid layer. These results are summarized in Table 1.

TABLE 1

Flat System Fluid Distribution Test - Co-apertured Material Matrix

|  | Apertured* 100 gsm, 0.06 g/cc, 80/20 | Apertured* 175 gsm, 0.08 g/cc, 88/12 | Apertured* 250 gsm, 0.14 g/cc, 90/10 | Control 250 gsm, 0.14 g/cc, 90/10 |
| --- | --- | --- | --- | --- |
| Stain Size | 12.7 cm | 10.2 cm | 10.2 cm | 15.2 cm |
| Saturation | Even Profile | Even Profile | Even Profile | Even Profile |
| Retention | 3.5 g | 3.8 g | 3.0 g | 4.5 g |
| Transfer | 2.5 g | 2.3 g | 3.0 g | 1.5 g |

*The densities reflected above are pre-apertured densities, the densities of the apertured materials are higher.

This testing showed a decrease in stain length as well as fluid retention in the apertured samples, compared to the control, indicating that aperturing the airlaid fabric increases the density of the airlaid dramatically because the pin density of the initial aperturing pattern (FIG. 8) was so high. This is most noticeable on high basis weight, high original density samples. As the density increases, the pore size and void volume decrease.

Figure 9:
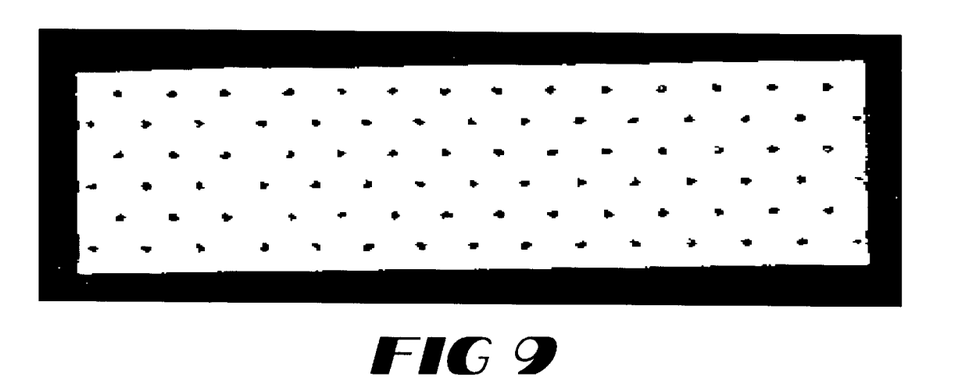
FIG. 9 shows the pin aperturing pattern at 2.5 pins/cm$^2$ with the same pin diameter.

As a result of this sample testing, it was determined that aperturing had the potential to impact product performance. Further testing was performed at a pin density of 16 pins/inch$^2$ (2.5 pins/cm$^2$) (shown in FIG. 9) to minimize increases in post-aperturing material density. The pin diameter remained at 0.081". The range of fabric density studied was narrowed to 175 to 200 gsm and the airlaid fabric was co-apertured to a spunbond fabric transfer delay layer to maintain the distribution functionality.

Tables 2 and 3 display the additional material matrices that were evaluated. The transfer delay layers were spunbond polypropylene fabrics except where film is indicated. The spunbond transfer delay layers had a density and basis weight as indicated. The spunbond fabrics were not treated with surfactants so remained naturally non-wettable. The film was a 1 mil thick polyethylene film.

TABLE 2

Co-apertured Airlaid Material/Transfer Delay Layer

| Basis Weight | Density | Transfer Delay Layer |
|---|---|---|
| 175 gsm | 0.08 g/cc | 27 gsm |
| 175 gsm | 0.08 g/cc | 33.9 gsm |
| 175 gsm | 0.10 g/cc | 27 gsm |
| 175 gsm | 0.10 g/cc | 33.9 gsm |

TABLE 3

Co-apertured Airlaid Material/Transfer Delay Layer

| Basis Weight | Density | Transfer Delay Layer |
|---|---|---|
| 175 gsm | 0.12 g/cc | 27 gsm |
| 175 gsm | 0.14 g/cc | 33.9 gsm |
| 200 gsm | 0.12 g/cc | 27 gsm |
| 200 gsm | 0.12 g/cc | 33.9 gsm |
| 200 gsm | 0.12 g/cc | Film |
| 200 gsm | 0.14 g/cc | 27 gsm |
| 200 gsm | 0.14 g/cc | 33.9 gsm |
| 200 gsm | 1.14 g/cc | Film |

The materials described in Tables 2 and 3 represent materials which were believed to have better performance characteristics potential due to lower aperturing pin density and lower basis weight and/or starting densities. These materials were tested for capacity, horizontal wicking capability, saturation capacity, fluid partitioning characteristics, and triple intake gush capability. Each of these areas is discussed individually below.

Capacity

Figure 10:
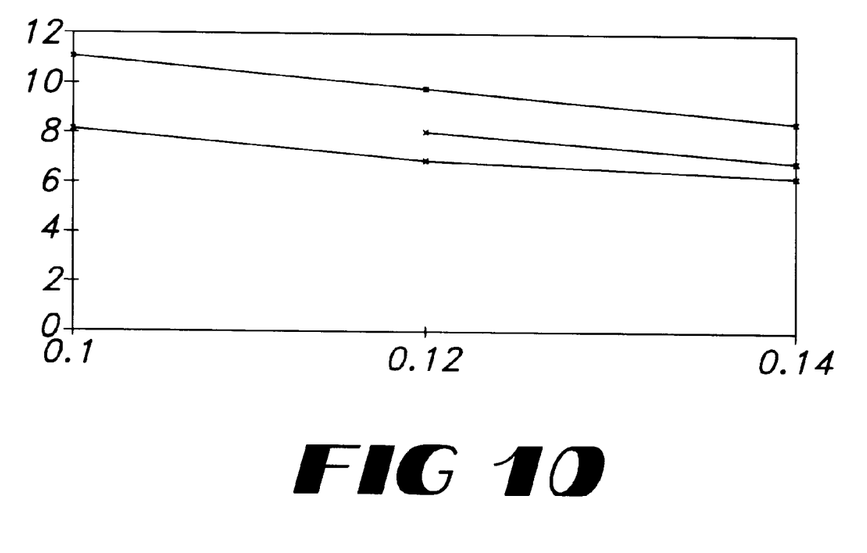
FIG. 10 is a graph the measured capacity for airlaid fabrics with and without apertures where capacity is on the Y-axis and fabric density (cc/g) on the X-axis.

FIG. 10 shows the measured capacity for airlaid fabrics with and without apertures where capacity is on the Y-axis and fabric density (cc/g) on the X-axis. In FIG. 10, the top line represents the 175 and 200 gsm, un-apertured airlaid fabrics, the middle line a 200 gsm co-apertured airlaid fabric, and the bottom line a 175 gsm co-apertured fabric. Capacity decreases with increasing density as expected. Capacity is also slightly reduced for the apertured samples. This data reveals that an apertured airlaid fabric at 200 gsm and 0.14 g/cc has an equivalent capacity to an un-apertured 175 gsm, 0.14g/cc fabric.

Horizontal Capillary Wickina—Infinite Reservoir

Horizontal capillary wicking testing was completed to assess the effect of the aperturing process on horizontal wicking distance. Horizontal wicking distance is important to maintain a visual signal which alerts the wearer that the product is nearing capacity and should be replaced. Without appropriate wicking functionality, the visual signal is not present to the desired degree.

Figure 11:
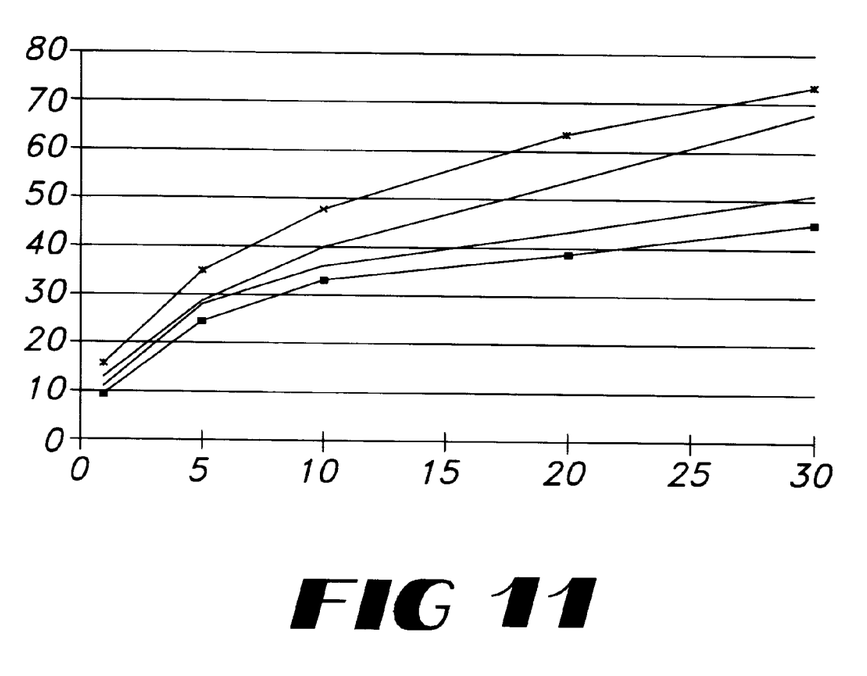
FIG. 11 is a graph of horizontal wicking distance (Y-axis) versus time for two apertured and two un-apertured airlaid fabrics.

The horizontal capillary wicking results of the 175 gsm low density airlaid samples of Table 2 indicate that aperturing the airlaid material reduces capillary wicking distance. Its believed that the aperturing process creates apertures which disrupt the fluid pathway for wicking and creates density gradients around each aperture. The apertured materials wicked between 17 and 30 mm less than the un-apertured samples, depending on original density. A larger difference existed for materials which had a higher starting density. These results are shown in FIG. 11 where wicking distance in mm is shown on the y-axis and time in minutes on the x-axis. In FIG. 11, the 33.9 gsm un-apertured fabric is the highest line, immediately below it is the line for the 27 gsm un-apertured fabric, followed by the 27 gsm apertured fabric and the 33.9 gsm apertured fabric.

FIG. 11 also indicates that the wicking path disruption associated with aperturing has more impact on horizontal wicking performance than the effect of increased airlaid density. This indicates that the aperturing effect is not a simple densification effect. The horizontal wicking results indicate that there is capillary discontinuity in the apertured samples which results in a significant wicking path disruption.

In an effort to improve wicking distance, higher density airlaid fabric samples were apertured and their capillary wicking performance evaluated. Again the results indicate that the higher density samples do not wick as far as the un-apertured control material. This further showed that capillary disruption is a result of the aperturing process and indicates that capillary wicking distance cannot be controlled by density in the apertured materials.

Horizontal Wicking Saturation Capacity

To assess the saturation level that results after the horizontal wicking test, the saturated materials were sectioned and weighed. The gram per gram saturation level was then calculated to determine how the aperturing process affects the overall gram per gram capacity level of the materials. Note that these saturation levels are based on capillary wicking and not on a dunk and drip protocol.

Figure 12:
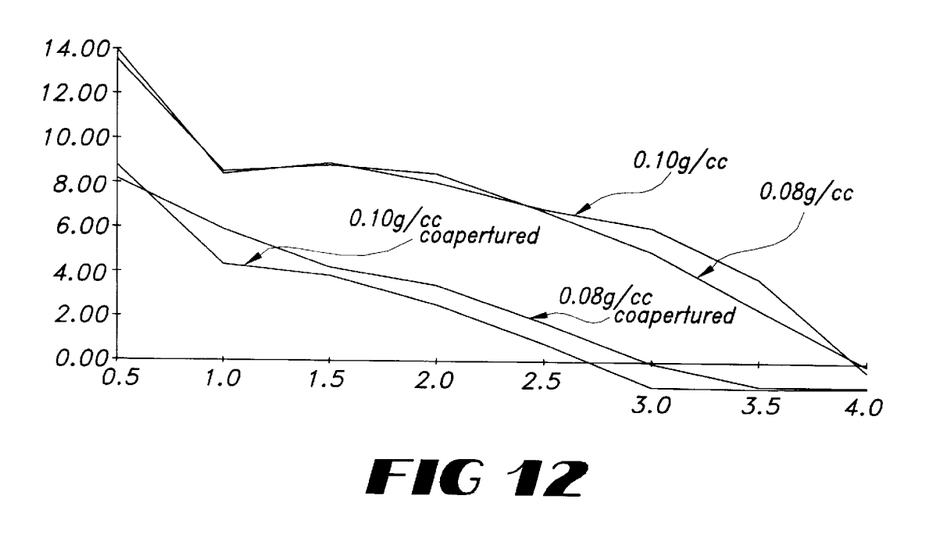
FIG. 12 is a graph of saturation in g/g (Y-axis) versus horizontal wicking distance in inches.

FIG. 12 displays the effect of aperturing on saturation level for the 175 gsm low density airlaid samples of Table 2. The results indicate that not only does horizontal wicking distance decrease as a result of the aperturing process, but wicking saturation capacity decreases also. The apertured samples are much less saturated than the un-apertured samples regardless of starting density though no significant differences were noted between samples that had different starting densities. The effect of aperturing was appeared to be more dominant than the effect of starting density. In FIG. 12, the saturation in g/g is indicated on the y-axis and the wicking distance in inches on the x-axis. The upper most line represents the un-apertured 0.1 g/cc sample, the line below the 0.08 g/cc un-apertured sample, the next line down represents the 0.08 g/cc co-apertured sample and the lowest line the 0.1 g/cc co-apertured sample.

The effect of aperturing on the capillary wicking saturation of higher density airlaid materials was also assessed. Again, the apertured samples had lower gram per gram saturation levels than the un-apertured control. It thus appears that basis weight had a minimal effect on horizontal wicking distance or saturation level of the co-apertured samples. The 175 and 200 gsm samples perform similarly and only slight differences were noticed between densities.

Overall wicking distance was the same for 0.12 and 0.14 g/cc samples, but the saturation level of the 0.12 g/cc samples was higher, believed to be attributable to the higher void volume of the 0.12 g/cc samples.

Since products experience a variety of pressures and flow conditions in use, wicking potential under demand absorbency was also studied. The results showed that the materials are evenly saturated throughout their length, indicating that wicking is not decreased by aperturing in a demand absorbency wicking setting. Its believed that the stable structure of the airlaid fabric allows the apertured airlaid fabric to be fully utilized even though it does not have the continuous capillary fluid paths that are found in an un-apertured airlaid fabric.

As a result of this testing, its believed that the pin density should be between about 10 and 40 pins/inch$^2$ (1.6 and 6.2 pins/cm$^2$) for good performance. Optimal pin density will depend on the exact product form into which the inventive laminate is placed.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

It should further be noted that any patents, applications or publications referred to herein are incorporated by reference in their entirety.

What is claimed is:

1. An intake/distribution layer for personal care products comprising co-apertured distribution and nonwoven transfer delay layers, wherein said transfer delay layer controls fluid movement in a Z-direction of said product and wherein said co-aperturing produces apertures with walls wherein liquid can be absorbed through the walls of said apertures.

2. The layer of claim 1 wherein said co-apertured materials were apertured with pins at a density of between about 1.6 and 6.2 pins/cm$^2$.

3. The layer of claim 2 wherein said co-apertured materials were apertured with pins at a density of about 2.5 pins/cm$^2$.

4. The layer of claim 1 wherein said transfer delay layer is a material selected from the group consisting of nonwoven fabrics and films.

5. The layer of claim 1 wherein said distribution layer horizontally wicks menses a distance of from about 1.2 cm to about 15.25 cm.

6. The layer of claim 5 wherein said distribution layer is a material selected from the group consisting of airlaid fabric, bonded carded webs, coform materials, hydroentangled pulp fabrics and meltblown fabrics.

7. A personal care product selected from the group consisting of diapers, training pants, absorbent underpants, adult incontinence products and feminine hygiene products comprising the layer of claim 1.

8. The product of claim 6 wherein said personal care product is a feminine hygiene product.

9. The product of claim 6 wherein said personal care product is an adult incontinence product.

10. The product of claim 6 wherein said personal care product is an adult incontinence product.

11. An intake/distribution layer for personal care products comprising co-apertured distribution and nonwoven transfer delay layers, wherein said transfer delay layer controls fluid movement in a Z - direction of said product, wherein said co-aperturing produces apertures with walls wherein liquid can be absorbed through the walls of said apertures, and wherein said distribution layer comprises staple polyolefin and is produced by the airlaying process onto said transfer delay layer, and wherein said layers are apertured at a pin density of between about 1.6 and 6.2 pins/cm$^2$.

12. The layer of claim 10 wherein said co-apertured materials were apertured with pins at a density of about 2.5 pins/cm$^2$.

13. The layer of claim 10 wherein said airlaid layer is comprised of pulp and thermoplastic fibers.

14. The layer of claim 10 wherein said transfer delay layer comprises polyolefin fiber produced by the spunbonding process.

15. The layer of claim 13 wherein said polyolefin is polypropylene.

16. The layer of claim 10 wherein said transfer delay layer comprises polyolefin film.

17. The layer of claim 15 wherein said polyolefin is polyethylene.

* * * * *